United States Patent [19]

Becker et al.

[11] 4,276,090
[45] Jun. 30, 1981

[54] METHOD FOR PROTECTING INDUSTRIAL SUBSTRATES FROM FUNGAL OR BACTERIAL ATTACK

[75] Inventors: Frank C. Becker, Gurnee; Jorge P. Li, Libertyville, both of Ill.

[73] Assignee: Abbott Laboratories, North Chicago, Ill.

[21] Appl. No.: 959,549

[22] Filed: Nov. 13, 1978

Related U.S. Application Data

[62] Division of Ser. No. 843,610, Oct. 19, 1977, Pat. No. 4,141,905.

[51] Int. Cl.³ .............................................. C09D 5/14
[52] U.S. Cl. ............................. 106/18.32; 106/163 R; 424/274; 427/394
[58] Field of Search .......................... 260/326.5 FM; 106/18.32, 163 R; 424/274; 427/394

[56] References Cited

U.S. PATENT DOCUMENTS

| | | | |
|---|---|---|---|
| 2,444,536 | 7/1948 | Searle | 260/326.5 FM |
| 4,111,879 | 9/1978 | Mori et al. | 106/16 |
| 4,130,433 | 12/1978 | Becker et al. | 260/326.5 FM |

*Primary Examiner*—Lorenzo B. Hayes
*Attorney, Agent, or Firm*—Paul D. Burgauer; Robert L. Niblack

[57] ABSTRACT

Method for protecting fabrics, plastics, paints, etc. from fungal and/or bacterial attack comprising treating same with N-(2-methyl-1-naphthyl) maleimide.

2 Claims, No Drawings

METHOD FOR PROTECTING INDUSTRIAL SUBSTRATES FROM FUNGAL OR BACTERIAL ATTACK

This is a division, of application Ser. No. 843,610, filed Oct. 19, 1977, now U.S. Pat. No. 4,141,905.

DETAILED DESCRIPTION OF THE DISCLOSURE

Synthetic, film-forming materials, such as those used in the manufacture of plastic films and woven fibrics made from synthetic or cellulosic fibers are known to be subject to bacterial or fungal attacks. This is particularly known to those manufacturers whose products will be used on exterior surfaces and/or under conditions that are prone to host undesirable fungal and bacterial micro-organisms.

In order to prevent bacterial or fungal attack and consequent deterioration of the polymeric or cellulosic material so attacked or the substrate to which they are applied, manufacturers of plastic films or woven fabrics have used a number of biocides on a routine basis. Many of the currently used industrial biocides are organometallics, such as arsenicals; they are highly successful in preventing bacterial or fungal deterioration of plastics. For environmental reasons, however, organometallics are now less accepted in some of the industrial uses where biocides are needed. It has thus become highly desirable to find new, non-metallic biocides that provide protection for polymeric substrates of all types, including film-formers, plastics, cellulosics, and the like.

It has now been found that a cellulosic, plastic or film-forming polymeric composition, knitted, woven, molded or extruded into a continuous form can be protected against bacterial or fungal attacks by treating such substrates with the new compound of the current invention: N-(2-methyl-napthyl)maleimide. The new compound is a homolog of a compound in U.S. Pat. No. 2,444,536, but unlike the N-(1-naphthyl)-maleimide described there as a fungicide and insecticide, the current compound, in addition to the expected fungicidal activity, has strong antibacterial properties. Thus, the new compound is a potent and highly useful industrial biocide; it can easily be incorporated into or applied to the surface of plastics, polymers, cellulosics and similar organic substrates. At concentrations of 0.005–5.0% by weight, the new compound will completely protect said substrates against bacteria or fungi often found in the environment. Furthermore, in contrast to commonly used industrial biocides including arsenicals, the new biocide does not lose its activity when exposed to UV-light.

When a substrate is treated with the new compound of this invention, growth of bacteria or fungi also is inhibited in areas in contact with the surface of said treated substrate, particularly when said compound is present in the higher range of the concentration recited above.

For the purpose of the present description, the term "film-forming" should be understood to refer to the polymeric particles, whether those particles are present as dry, particulate matter or in liquid, dissolved, suspended, coherent, continuous or any other form, particularly including the ultimate form for which said particles are designed. The term "plastic" is used in a similarly broad version and is to be understood to include those polymeric materials which can be extruded, injection- or compression-molded into the desired ultimate shape. The term "cellulosic" is primarily designed to refer to cotton, but also includes those cellulosic derivatives wherein the basic cellulosic structure of the fibrous material has undergone some chemical modifications that do not materially change the number of repeating units in the cellulose structure.

The current biocide is particularly useful for the treatment of leather, leather substitutes, wood or plastic products, or fabrics made from cellulosic or olefin polymers, knitted, woven, extruded or molded into structures exposed to outdoor conditions, such as outdoorwear, tents, boots, belts, tarpaulins, swimming pool liners and the like. The new biocide can similarly usefully be employed as an additive to industrial fluids, e.g., cooling water, hydrocarbon fluids, metal cutting fluid; it also can be incorporated for its biocidal effect into cosmetics and, of course, paints of all types, including alkyd, oil-based or latex paints.

In a general embodiment, the compound of the current invention is made by heating maleic anhydride with about a equimolar amount of 2-methyl-1-napthylamine in the presence or absence of 0.2–1.6 liters of a lower fatty acid per mole of reactants for at least 30 minutes, preferably 1–5 hours. When operating in the absence of a solvent, temperatures of 130°–190° C. are best suited; where a solvent is used, temperatures of between 100° C. and the boiling point of the solvent give best results. Only lower fatty acids, particularly glacial acetic, propionic and butyric acids are suitable as reaction media. Other solvents only produce the corresponding maleamic acid without ring closure. After the product crystallizes out upon cooling, the crystalline mass is collected by filtration, washed with ethanol or water and dried in vacuo. In the cases where no crystalline product separates upon cooling, part or all of the acid solvent is removed from the reaction solution by vacuum-distillation or evaporation in vacuo. The residue can then be triturated with dilute alcohol or water to give crystalline N-(2-methyl-1-naphthyl)maleimide. Again, the solid is collected by filtration, washed with dilute alcohol or water, and dried at 50° C. over $P_2O_5$ in vacuo.

Normally, the product obtained in the above manner is pure enough for use as an industrial biocide. However, if further purification is desired, the above compound can readily be purified either by recrystallization or column chromatography. For recrystallization, the following solvents or combination thereof are most suitable: lower alcohols, particularly methanol, ethanol, 2-propanol, aqueous alcohol, ethyl acetate, acetic acid, methylene chloride, chloroform, petroleum ether, benzene, toluene, acetone, dimethylformamide, dimethylsulfoxide. For column chromatography, both silica gel and neutral aluminum oxide can be used with excellent results. The best solvents or solvent combinations for elution are chloroform, methylene chloride, ethyl acetate, benzene, toluene, and petroleum ether or compatible mixtures thereof.

The effect of the above new biocide is best understood by reference to a general embodiment: To a film-forming mixture containing a synthetic polymeric material which is to be processed into a continuous phase and contains the usual ingredients, such as dyes, pigments, plasticizers, preservatives and the like, is added between 0.005 and 5.0% by weight of N-(2-methyl-1-naphthyl)maleimide and all ingredients are dispersed to form a homogeneous mass. Such a mixture is stable under normal storage conditions; it can be stored for extended periods of time under conditions usually required for such materials. The shaped article made from or coated with this mixture is then resistant to fungal or bacterial attack. This is the case whether said article is obtained by compression-molding, injection-molding, extrusion or whether it is a surface film as obtained by applying a coating formulation through brushing, spray-coating or dipcoating onto the substrate and subsequent drying. These coating methods primarily are applicable where the continuous substrate is a woven or knitted cellulosic material or wood. In most instances, the substrate and areas in contact therewith are also protected from deterioration by bacterial or fungal attack.

In order to illustrate the preparation and use of N-(2-methyl-1-naphthyl)maleimide in connection with a film-forming or plastic mixture or a woven fabric, reference is made to the following examples which, however, are not intended to limit the invention in any respect.

EXAMPLE 1

A solution of 538 g. of 2-methyl-1-naphthylamine in 700 ml. of glacial acetic acid is placed in a 3-liter, three-necked flask equipped with stirrer, a reflux condenser and thermometer. To this solution is added a solution of 373 g. of maleic anhydride in 500 ml. of glacial acetic acid in a slow stream under vigorous stirring. The mixture is heated at reflux for 3 hours. Upon subsequent cooling to room temperature and occasional agitation to induce crystallization, N-(2-methyl-1-naphthyl)maleimide crystallizes and is collected by filtration. The material is sucked almost dry and washed with 95% aqueous ethanol and a large amount of water. It is dried in a vacuum oven at 80°–110° C. for 8 hours, producing 623 g. (76.8%) theory of a technically pure sample as a light yellow, crystalline powder, melting at 156°–8° C.

By using larger quantities of glacial acetic acid, essentially the same results are obtained at 1–10 hours of heating. However, when the heating time is shorter than 1 hour, the yield is reduced.

When the above reaction is carried out in the absence of a solvent at temperatures of 130°–190° C., the reaction mixture solidifies upon cooling and the desired product is purified by recrystallization from ethanol or dilute ethanol.

In both instances, higher reaction temperatures and shorter reaction times produce about the same yield as lower temperatures and longer reaction times.

EXAMPLE 2

In tests wherein cotton fabric samples are dip-coated in an aqueous solution to absorb 0.5% by weight of the new compound, incubating said samples in nutrient agar for 24 hours at 37° C. with bacteria pink stain or mixed spores (*A. niger, A. flavus, C. globosum* and *P. funiculosum*) for 14 days at 31° C. and 90% humidity, it is shown in Table I, column A that excellent protection is obtained. In most instances, protection is also obtained in areas surrounding and directly in contact with the cotton fabrics; also, in many instances, similarly good results are obtained after exposing the samples for 24 hours to UV-light (Column B).

TABLE I

|  | A | B |
|---|---|---|
| *Staph. aureus* | 7/NGCA | 6/NGCA |
| *K. pneumoniae* | 1/NGCA | 0/GCA |
| Pink Stain | 7/NS | 5/NS |
| Mixed Spores | 2/NG | 0/NG |

NG = No growth
CA = Contact area
GCA = Growth in CA
NS = No stain
Number preceeding above abbreviations denotes the size of the protected area in mm.

EXAMPLE 3

Cotton samples containing 0.5% of N-(2-methyl-1-naphthyl)maleimide are placed horizontally on a 4-inch layer of soil and covered with a 1-inch layer of loosely packed soil. The soil "sandwiches" are placed in a humidity chamber for 14 days at 30° C. and 90% relative humidity, and the fabrics are then inspected visually. The recovered samples, after this severe test, are in excellent condition and show no sign of degradation.

EXAMPLE 4

Film strips are made from polyvinylchloride, containing the usual plasticizer, color stabilizer, preservative, UV stabilizer and 0.5% by weight of the above compound. They are tested in the usual fashion and after being exposed up to 300 hours in a Weather-Ometer with intermittent water spray and subsequent inoculation with some of the bacteria or mixed spores mentioned above. The results are given below in a comparison with those of the closest homolog, N-(1-naphthyl)-maleimide, and one of the best commercially available biocides, 10,10'-oxybisphenoxarsine (marketed as Vinyzene ® by Ventron), all at the 0.5% load level.

TABLE II

|  | New Compound | | | | Homolog | | Vinyzene | | | |
|---|---|---|---|---|---|---|---|---|---|---|
|  | 0 | 100 | 200 | 300 | 0 | 100 | 0 | 100 | 200 | 300 hrs. |
| *Staph. aureus* | 7/NGCA | 6/NGCA | 6/NGCA | 5/NGCA | 5/NGCA | 4/NGCA | 9/NGCA | 8/NGCA | 5/NGCA | 2/NGCA |
| *K. pneumonia* | 0.5/NGC | 0.5/NGC | 0/NGCA | 0/NGCA | 0.5/NG-CA | 0/GCA | 8/NGCA | 7/NGCA | 1/NGCA | 0/NGCA |
| Pink Stain | 8/NS | 7/NS | 7/NS | 6/NS | 4/NS | 6/NS | 8/NS | 5/NS | 3/NS | 0/HS |
| Mixed Spores | 3/NG | 2/NG | 1/NG | 0.5/NG | 0.5/NS | 0/NG | 14/NG | 8/NG | 3/NG | 0/TRG |

TRG = Trace growth
HS = Heavy stain

It is of particular interest to note that with Gram-negative *K. pneumoniae*, the current compound is highly effective while its homolog N-(1-naphthyl)maleimide fails at 100 hours of UV-exposure. The new compound also compares very favorably to Vinyzene and excells over the latter in all challenges after 300 hours of UV-light.

EXAMPLE 5

Wooden tongue depressors are dipped into the vinyl-acrylic paint compounds made according to the following method.

| Water | 250 parts |
|---|---|
| Anionic surfactant | 8 parts |

| -continued | |
|---|---|
| Non-ionic surfactant | 2.5 parts |
| Tetrapotassium phosphonate | 1 part |
| Hydroxyethylcellulose | 2.5 parts |
| Ethylene glycol | 25 parts |
| Cellulose acetate | 15 parts |
| Defoamer | 3 parts |
| Titanium dioxide | 175 parts |
| Magnesium silicate | 250 parts |
| Biocide | 5 lbs./100 gals. |

The above ingredients are dispersed for 20 minutes and then blended with 400 parts of a vinyl-acrylic emulsion (sold as UCAR by Union Carbide) and 1 part of a defoamer.

After the paint is dried, the painted surface is inoculated with a mixture of *A. pullulans, P. funiculosum* and *A. niger,* containing 10,000 spores/ml of each. The samples are then placed in a mold box for a period of 4 weeks at 30° C. and 90% relative humidity. Table III shows a comparison of the paint samples with the current biocide, a control (no biocide) and a sample containing the same amount of Nopcocide ®N-96, a commercially accepted biocide. The ratings are: 0 for no growth on sample, 1 for 0–25% growth, 2 for 25–50% growth, 3 for 50–75% growth and 4 for 75–100% growth of spores over the painted surface. The ratings shown are for the three samples with each paint mixture tested.

TABLE III

| Sample | Rating | | |
|---|---|---|---|
| Control | 4 | 4 | 4 |
| N-(2-Methyl-1-naphthyl)maleimide | 0 | 0.5 | 0.5 |

TABLE III-continued

| Sample | Rating | | |
|---|---|---|---|
| Nopcocide ®N-96 | 1 | 0.5 | 1 |

EXAMPLE 6

Exposure panels are prepared by dividing 7"×36" white pine boards into six 7"×6" sections. Each of the sections is painted with a vinyl acrylic paint, either containing no biocide (blank) or containing a biocide at a specific concentration. The vinyl acrylic paints are prepared according to the formulation and method as described in Example 5.

The painted panels are dried and exposed in standard fashion in a field near San Juan, Puerto Rico. The conditions and the microbial growth on the panels are evaluated after exposure for four months. The paint emulsion containing 5 lbs./100 gal. N-(2-methyl-1-naphthyl)-maleimide shows a rating of 9, paint with 9 lbs./gal. of di(phenylmercury)-dodecenyl succinate shows a rating of 5 and paints containing no biocides rates 2 on a scale which assigns 10 to no bacterial or fungal growth and 0 shows complete overgrowth of the painted panels.

We claim:

1. The method of protecting a cellulosic, plastic or film-forming polymeric composition, knitted, woven, molded or extruded into a continuous form, against bacterial or fungal attack upon exposure to an environment containing common bacteria and fungi, comprising incorporating into said continuous form or coating said composition with a biocidally effective amount of N-(2-methyl-1-naphthyl)maleimide.

2. The method of claim 1 wherein said biocidally effective amount is between 0.005 and 5.0% by weight.

* * * * *